United States Patent
Mahmood et al.

(10) Patent No.: US 10,330,654 B2
(45) Date of Patent: Jun. 25, 2019

(54) METHODS FOR DETERMINING LOW SULFATE CONCENTRATIONS IN SYNTHETIC UREA SAMPLES, PRODUCED IN A MANUFACTURING PROCESS AND CONTAINING HIGH LEVELS OF IMPURITIES

(71) Applicant: SABIC Global Technologies B.V., PX Bergen Op Zoom (NL)

(72) Inventors: Khalid Mahmood, Jubail Industrial (SA); Naji Al-Haiz, Jubail Industrial (SA); Muhammad Khamees Al-Yousuf, Jubail Industrial (SA); Abdulrahim Ahmad Al-Rebeh, Jubail Industrial (SA)

(73) Assignee: SABIC Global Technologies B.V., PX Bergen Op Zoom (NL)

( * ) Notice: Subject to any disclaimer, the term of this patent is extended or adjusted under 35 U.S.C. 154(b) by 0 days.

(21) Appl. No.: 15/326,761

(22) PCT Filed: Jul. 17, 2015

(86) PCT No.: PCT/IB2015/055450
§ 371 (c)(1),
(2) Date: Jan. 17, 2017

(87) PCT Pub. No.: WO2016/012925
PCT Pub. Date: Jan. 28, 2016

(65) Prior Publication Data
US 2017/0212086 A1 Jul. 27, 2017

Related U.S. Application Data

(60) Provisional application No. 62/026,671, filed on Jul. 20, 2014.

(51) Int. Cl.
*G01N 30/88* (2006.01)
*C05C 9/00* (2006.01)
(Continued)

(52) U.S. Cl.
CPC ............ *G01N 30/88* (2013.01); *B01D 15/361* (2013.01); *C05C 9/005* (2013.01); *G01N 30/96* (2013.01);
(Continued)

(58) Field of Classification Search
CPC ........ G01N 30/24; G01N 30/34; G01N 15/05; G01N 15/04; G01N 30/02; G01N 30/74;
(Continued)

(56) References Cited

U.S. PATENT DOCUMENTS 2,035,557 A * 3/1936 Fritz ...................... A61K 38/24
424/546
3,785,796 A * 1/1974 Mann, Jr. ................ C05C 3/005
71/28
(Continued)

FOREIGN PATENT DOCUMENTS

| CN | 101574614 | 11/2009 |
| CN | 102351739 | 2/2012 |
| EP | 2662349 A1 | 11/2013 |

OTHER PUBLICATIONS

Putnam, Composition and concentrative properties of human urine, Jul. 1971, National Aeronautics and Space Administration.*
(Continued)

*Primary Examiner* — John Fitzgerald
*Assistant Examiner* — Truong D Phan
(74) *Attorney, Agent, or Firm* — Norton Rose Fulbright US LLP

(57) ABSTRACT

In one aspect, disclosed herein is a method for determining sulfate concentration in a sample, comprising: a) providing
(Continued)

a liquid sample comprising urea and at least one impurity; b) concentrating the liquid sample under conditions effective to reduce the liquid volume; c) forming a dilute sample solution by diluting the concentrated liquid sample of step b) in water; and d) analyzing the dilute sample solution of step c) with ion chromatography to determine if a concentration of sulfate is present in the provided liquid sample of step a); wherein the analyzing of step d) is capable of determining the presence of a sulfate concentration present in an amount less than about 1 ppm.

20 Claims, 1 Drawing Sheet

(51) Int. Cl.
  *G01N 30/96* (2006.01)
  *B01D 15/36* (2006.01)
(52) U.S. Cl.
  CPC ........... *G01N 2030/8809* (2013.01); *G01N 2030/8872* (2013.01); *G01N 2030/8886* (2013.01)
(58) Field of Classification Search
  CPC .. G01N 30/96; G01N 2030/965; G01N 30/56; A61B 5/15003; B01D 15/08; B01J 2220/54; B01J 20/32; C02F 1/281
  USPC ............. 73/61.65, 61.55; 436/161; 422/70; 210/198.2, 656, 660–694
  See application file for complete search history.

(56) References Cited

U.S. PATENT DOCUMENTS

| | | | | |
|---|---|---|---|---|
| 4,217,127 A * | 8/1980 | Kono | ............. | B01J 2/16 118/DIG. 5 |
| 4,306,029 A * | 12/1981 | Carpenter | ............. | A61F 5/441 435/268 |
| 4,385,632 A * | 5/1983 | Odelhog | ............. | A61L 15/46 422/5 |
| 4,690,100 A * | 9/1987 | Thomas | ............. | A01K 1/031 119/419 |
| 4,746,435 A * | 5/1988 | Onishi | ............. | B01D 53/22 210/615 |
| 5,122,446 A * | 6/1992 | Friedman-Kien | ............. | G01N 33/56988 435/5 |
| 5,132,018 A * | 7/1992 | Jones | ............. | G01N 30/34 210/198.2 |
| 5,137,626 A * | 8/1992 | Parry | ............. | B01D 11/043 210/198.2 |
| 5,192,690 A * | 3/1993 | Rust | ............. | G01N 30/461 436/106 |
| 5,529,935 A * | 6/1996 | Brink | ............. | G01N 30/06 436/111 |
| 5,596,948 A * | 1/1997 | Ritchie | ............. | A01K 1/031 119/417 |
| 5,599,374 A * | 2/1997 | Detrick | ............. | C05C 9/00 71/28 |
| 5,972,550 A * | 10/1999 | Tamura | ............. | G03G 5/144 430/131 |
| 6,129,892 A * | 10/2000 | Garrett | ............. | A61L 9/01 422/1 |
| 6,179,893 B1 * | 1/2001 | Bendix | ............. | C05C 3/00 71/28 |
| 6,492,144 B1 * | 12/2002 | Umansky | ............. | C12Q 1/6806 435/6.16 |
| 2002/0183814 A1 * | 12/2002 | Ono | ............. | A61F 7/0053 607/100 |
| 2003/0164015 A1 * | 9/2003 | Pildysh | ............. | C05D 9/00 71/31 |
| 2004/0101464 A1 * | 5/2004 | Brooks | ............. | C01C 1/08 423/355 |
| 2004/0235187 A1 * | 11/2004 | LaCourse | ............. | G01N 30/88 436/177 |
| 2007/0119341 A1 * | 5/2007 | Kitayama | ............. | C07D 249/06 106/31.47 |
| 2008/0199541 A1 * | 8/2008 | Tomaselli | ............. | A61K 9/0019 424/696 |
| 2009/0007643 A1 * | 1/2009 | Svensson | ............. | B01D 15/206 73/61.53 |
| 2009/0209474 A1 * | 8/2009 | Roegel | ............. | A61K 31/198 514/23 |
| 2009/0212206 A1 * | 8/2009 | Shiea | ............. | H01J 49/0431 250/282 |
| 2011/0020943 A1 * | 1/2011 | Okamoto | ............. | G01N 21/78 436/73 |
| 2011/0318814 A1 * | 12/2011 | Kshirsagar | ............. | C12M 47/04 435/239 |
| 2012/0252040 A1 * | 10/2012 | Yoon | ............. | G01N 33/57434 435/7.92 |
| 2014/0008303 A1 * | 1/2014 | Boyer | ............. | B01J 47/022 210/670 |
| 2014/0037570 A1 * | 2/2014 | Whitehurst | ............. | C05C 9/005 424/76.6 |
| 2014/0286890 A1 * | 9/2014 | Sookram | ............. | A61L 9/01 424/76.8 |
| 2016/0243175 A1 * | 8/2016 | Bushman | ............. | A61K 35/747 |

OTHER PUBLICATIONS

Denis et al, Note on the carbon dioxide content of urine, Apr. 1918, Chemical Laboratory of the Massachusetts General Hospital.*
Farahbakhshazad et al., Ammonia removal processes for urine in an upflow macrophyte system, 1997, American Chemical Society.*
Slyke, Determination of urea by gasometric measurement of the carbon dioxide formed by the action of urease, Apr. 1927, Hospital of the Rockefeller Institute for Medical Research.*
CSUS-Chemistry 31, Dilution factor, Sep. 2012.*
Merriam-Webster, concentrate thesaurus, Jun. 2012.*
"Understanding exhaust gas treatment systems: Guidance for shipowners and operators," Lloyd's Register. 71 Fenchurch Street, London EC3M 4BS, Jun. 2012, pp. 1-55.
"Determining Chloride and Sulfate Contents in Soil," Test Procedure, Texas D.O.T. Designation: TEX-620-J, Aug. 2005, pp. 1-11.
Bowen, J., "Develop a Quantitative Analytical Method for low (~ 1 ppm) levels of Sulfate," *Cantaurus*, vol. 7, pp. 5-8, May 1999.
Politi, et al., "Oxalate, phosphate and sulphate determination in serum and urine by ion chromatography," Clinica Chimica Acta. 184 (1989) 155-166.
Roos, W., "Granulation of Urea: Diamonds, Pearls and Stamicarbon Granules," Fertilizer Focus, May/Jun. 2013, pp. 1-4.
International Search Report and Written Opinion dated Oct. 13, 2015 for application PCT/IB2015/055450, filed on Jul. 17, 2015, and published as WO 2016/012925 (Applicant—SABIC Global Technologies B.V. // Inventor—Mahmood, et al.) (17 pages).

* cited by examiner

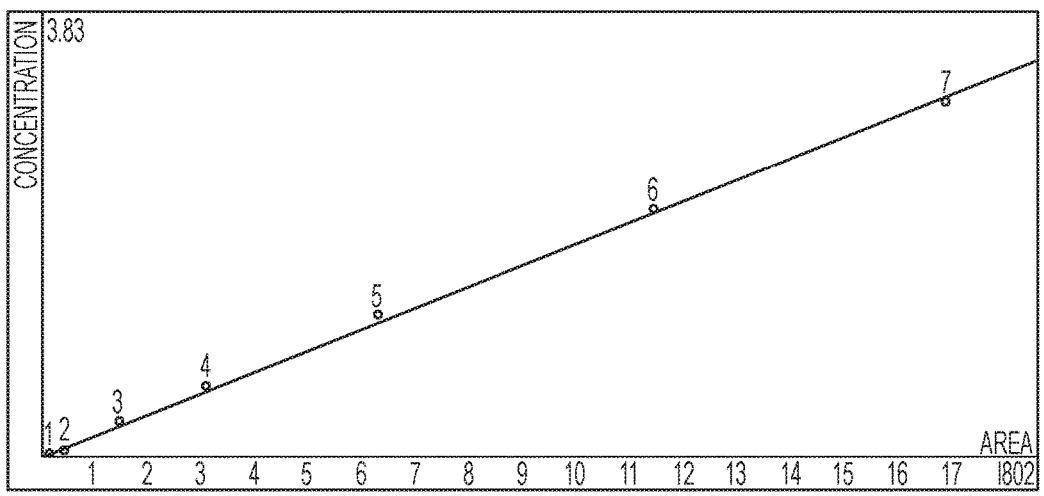
CALIBRATION OF COMPONENT SULPHATE
METHOD:                ANION SO4 IN UREA-1.MTW
EQUATION:              Q = 0.0301136.A
RSD:                   4.327%
CORRELATION COEFFICIENT: 0.999432
K3 = 0      K2 = 0      K1 = 0.0301136      K0 = 0
BASE:          AREA
REF.CHANNEL:   CH1
ISTD:
FORMULA:       LINEAR THROUGH ZERO
WEIGHT:        1
| LEVEL | HEIGHT | AREA  | CONC. | VOL/DIL | RETENTION | USED | FILE         |
|-------|--------|-------|-------|---------|-----------|------|--------------|
| 1     | 0.4213 | 15.85 | 0.005 | 100     | 18.5      | YES  | X7192038.CHW |
| 2     | 1.143  | 42.25 | 0.01  | 100     | 18.5      | YES  | X7191801.CHW |
| 3     | 3.88   | 146.1 | 0.05  | 100     | 18.5      | YES  | X7191828.CHW |
| 4     | 8.254  | 307.4 | 0.1   | 100     | 18.5      | YES  | X7191852.CHW |
| 5     | 17.08  | 628.3 | 0.2   | 100     | 18.5      | YES  | X7191919.CHW |
| 6     | 31.46  | 1145  | 0.35  | 100     | 18.5      | YES  | X7191945.CHW |
| 7     | 47.02  | 1691  | 0.5   | 100     | 18.5      | YES  | X7192012.CHW |

METHODS FOR DETERMINING LOW SULFATE CONCENTRATIONS IN SYNTHETIC UREA SAMPLES, PRODUCED IN A MANUFACTURING PROCESS AND CONTAINING HIGH LEVELS OF IMPURITIES

CROSS REFERENCE TO RELATED APPLICATIONS

This is a U.S. National Phase Application of International Application No. PCT/IB2015/055450, filed Jul. 17, 2015, which claims the benefit of and priority to U.S. Provisional Application No. 62/026,671, filed on Jul. 20, 2014, which are both hereby incorporated by reference in their entirety.

BACKGROUND

To comply with industry regulations, scrubbers are typically installed in urea plants to capture and reduce ammonia and urea dust particles that can be present in exhaust gases from the granulator stack. Usually, scrubbers are vertically-disposed vessels with chimney tray stages and/or mist eliminators. Recirculated urea solution enters at the top of the dust removal section and flows down by gravity while the off-gas enters at the bottom of the scrubber and flows upwards in a countercurrent direction. On its way down, the liquid flows horizontally over the trays or mist eliminators and comes into contact with the off-gas rising through the tray openings, capturing its content of urea dust. Another kind of scrubber utilizes sulfuric acid to capture the NH3 in the off-gas as the respective ammonium salt (AS).

With these conventional scrubbers, however, there is a chance for seepage of sulfate back upstream into other sections of the urea plant, such as the urea granulator or urea synthesis sections. Excess sulfate seepage upstream can lead to corrosion damage to plant parts and can also result in the manufacture of product that is out of desired specification. As such, it is necessary to monitor the slippage of sulfate to the different urea plant sections. Current methods are unable to detect sulfate concentrations present in urea samples at levels of 1 ppm and below. Moreover, the samples that are tested are complicated samples with relatively high concentration of urea, ammonia ($NH_3$), and carbon dioxide ($CO_2$). Thus, there remains a need for improved methods for detecting and measuring sulfate concentrations that are capable of determining sulfate concentrations present in an amount less than 1 ppm, while also being capable of detecting and determining sulfate content in complicated samples with high concentration of urea, ammonia, and carbon dioxide.

SUMMARY

In accordance with the purposes of the present invention, as embodied and broadly described herein, the invention, in one aspect, provides a method for determining sulfate concentration in a sample. According to aspects, the sample can originate from a urea manufacturing process. The method generally comprises first providing a liquid sample comprising urea and at least one impurity. The liquid sample is concentrated under conditions effective to reduce the liquid volume of the sample. A dilute sample solution is formed by diluting the concentrated liquid sample in water. The dilute sample solution is analyzed with ion chromatography to determine if a concentration of sulfate is present in the provided liquid sample. According to aspects, the method, and more specifically, the analyzing step, is capable of determining the presence of a sulfate concentration present in an amount less than about 1 ppm.

In a further aspect, the invention also provides a method comprising providing a solid sample comprising urea and at least one impurity. A dilute sample solution is formed by dissolving the solid sample in water. The dilute sample solution is analyzed with ion chromatography to determine if a concentration of sulfate is present in the provided solid sample. According to aspects, the method, and more specifically, the analyzing step, is capable of determining the presence of a sulfate concentration present in an amount less than about 1 ppm.

In a yet further aspect, the present invention also provides a method comprising providing a process sample comprising urea and sulfate. The process sample is analyzed with ion chromatography to determine the sulfate concentration in the process sample. According to aspects, the method, and more specifically, the analyzing step, is capable of determining the presence of a sulfate concentration present in an amount less than about 1 ppm.

Additional advantages of the present invention will be set forth, in part, in the description which follows and, in part, will be obvious from the description or can be learned by practice of the present invention. The advantages of the present invention will be realized and attained by means of the elements and combinations particularly pointed out in the appended claims. It is to be understood that both the foregoing general description and the following detailed description are exemplary and explanatory only and are not restrictive of the present invention, as claimed.

BRIEF DESCRIPTION OF THE FIGURES

The accompanying figures, which are incorporated in and constitute a part of this specification, illustrate several aspects and together with the description serve to explain the principles of the invention.

FIG. 1 shows a representative sulfate calibration curve according to the methods of the present invention.

DETAILED DESCRIPTION

The present invention can be understood more readily by reference to the following detailed description of the invention and the examples included therein.

Before the present compositions, articles, systems, devices, and/or methods are disclosed and described, it is to be understood that they are not limited to specific methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds and compositions can be given using common names as well as names assigned by the International Union of Pure and Applied Chemistry (IUPAC), Chemical Abstracts Service (CAS) recommendations for nomenclature, hereby incorporated herein by reference. One of skill in the art can readily ascertain the structure of a compound and composition if given a name by systemic reduction of the compound structure using naming conventions.

As used in the specification and the appended claims, the singular forms "A," "an," and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component denotes the weight relationship between the element or component and any other elements or components or article for which a part by weight is expressed. Thus, in a composition comprising two parts by weight of component X and five parts by weight component Y, X and Y are present at a weight ratio of 2:5 or 2/5 or 0.4, and are present in such ratio regardless of whether additional components are contained in the compound. Additionally, references in the specification and concluding claims to molar ratios of a particular element or component denotes the molar relationship between the element or component and any other elements or components in the composition or article for which a molar ratio is expressed. Thus, in a composition containing five moles of component X and two moles component Y, X and Y are present at a molar ratio of 5:2 or 5/2 or 2.5 and are present in such ratio regardless of whether additional components are contained in the composition.

A weight percent (wt. %) of a component, unless specifically stated to the contrary, is based on total weight of the formulation or composition in which the component is included.

As used herein, the terms "optional" or "optionally" means that a subsequently described event or circumstance can or cannot occur, and that the description includes instances where said event or circumstance occurs and instances where it does not.

It is known that chemical substances form solids which are present in different states of order which are termed polymorphic forms or modifications. Different modifications of polymorphic substances can differ greatly in their physical properties. Urea granule compositions can comprise different polymorphic forms, with it being possible for particular modifications to be metastable. Unless stated to the contrary, the present invention includes all such possible polymorphic forms.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow, plain meaning derived from grammatical organization or punctuation, and number or type of embodiments described in the specification.

Disclosed are components to be used to prepare compositions as well as the compositions themselves to be used within the methods disclosed herein. These and other compounds are disclosed herein, and it is understood that when combinations, subsets, interactions, groups, etcetera, of these materials are disclosed that while specific reference of each various individual and collective combinations and permutation of these components cannot be explicitly disclosed, each is specifically contemplated and described herein. For example, if a particular composition is disclosed and discussed and a number of modifications that can be made to a number of compounds including the compositions are discussed, specifically contemplated is each and every combination and permutation of the composition and modifications that are possible unless specifically indicated to the contrary. Thus, if a class of compounds A, B, and C are disclosed as well as a class of compositions D, E, and F and an example of a composition, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using compositions. Thus, if there are a variety of additional steps that can be performed, it is understood that each of these additional steps can be performed with any specific embodiment or combination of embodiments of the methods of the invention.

B. Methods for Determining Sulfate Concentration

1. Overview of Urea Production Process

In various aspects, commercial manufacture of urea is from carbon dioxide and ammonia. The reaction proceeds in two steps, first with the formation of carbamate and second with the dehydration of carbamate into urea and water. Briefly, urea is synthesized starting from $CO_2$ and $NH_3$ as raw materials. Under the proper operating parameters (temperature and pressure), $CO_2$ and $NH_3$ can combine into carbamate, and simultaneously dehydrate to give urea and water. The reaction is in two steps:

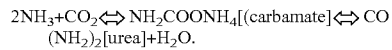
$$2NH_3 + CO_2 \Leftrightarrow NH_2COONH_4 \text{[(carbamate]} \Leftrightarrow CO(NH_2)_2 \text{[urea]} + H_2O.$$

Urea particles or granules can then be produced using prilling and/or granulation. Prilling is performed in a prilling tower wherein a urea-comprising liquid is sprayed in the form of fine droplets. On their way down these droplets are cooled and solidified by rising air. At the bottom of the prilling tower the solid particles are collected. Granulation of a urea-comprising liquid can take place in different types of granulation equipment. Seed particles are added to the granulation equipment and are kept moving within the granulation equipment. The urea-comprising liquid is sprayed over the seed particles and cooled. In this way the seed particles grow to obtain urea granules.

The above-described processes form fine dust during the spraying of the urea-comprising solution, and is collected into the cooling air. The large amount of cooling air used during prilling and granulation must be cleaned of most of the dust before it can be discharged into the environment.

Scrubbers are installed in urea plants to capture and reduce urea dust particles and ammonia in exhaust gases from the granulator stack. Usually, scrubbers are vertically-disposed vessels with chimney tray stages and/or mist eliminators. Recirculated urea solution enters at the top of the dust removal section and flows down by gravity while the off-gas enters at the bottom of the scrubber and flows upwards in countercurrent. On its way down, the liquid flows horizontally over the trays or mist eliminators and comes into contact with the off-gas rising through the tray openings, capturing its content of urea dust. Another kind of scrubber utilizes sulfuric acid to capture the NH3 in the off-gas as the respective ammonium salt (AS). However, with these scrubbers, there is a chance for seepage of sulfate back upstream into other sections of the urea plant, such as the urea granulator or urea synthesis sections. Excess sulfate seepage upstream can lead to corrosion damage to plant parts and out of specification product.

2. Methods for Determining Sulfate Concentration in Urea Samples

In various aspects, the present invention relates to methods for determining sulfate concentration in a sample. According to aspects, the sample can originate from a urea manufacturing process. The sample is analyzed with ion chromatography to determine if a concentration of sulfate is present in the provided sample. According to further aspects, the method, and more specifically, the analyzing step, is capable of determining the presence of a sulfate concentration present in an amount less than about 1 ppm.

In one aspect, the present invention provides a method for determining sulfate concentration in a sample, comprising: a) providing a liquid sample comprising urea and at least one impurity; b) concentrating the liquid sample under conditions effective to reduce the liquid volume; c) forming a dilute sample solution by diluting the concentrated liquid sample of step b) in water; and d) analyzing the dilute sample solution of step c) with ion chromatography to determine if a concentration of sulfate is present in the provided liquid sample of step a); wherein the analyzing of step d) is capable of determining the presence of a sulfate concentration present in an amount less than about 1 ppm.

In a further aspect, the present invention also provides a method for determining sulfate concentration in a sample, comprising: a) providing a solid sample comprising urea and at least one impurity; b) forming a dilute sample solution by dissolving the solid sample of step a) in water; and c) analyzing the dilute sample solution of step b) with ion chromatography to determine if a concentration of sulfate is present in the provided solid sample of step a); wherein the analyzing of step c) is capable of determining the presence of a sulfate concentration present in an amount less than about 1 ppm.

In a yet further aspect, the present invention also provides a method for determining sulfate concentration in a sample, comprising: a) providing a process sample comprising urea and sulfate; and b) analyzing the process sample with ion chromatography to determine the sulfate concentration in the process sample; wherein the analyzing of step b) can determine sulfate concentration present in the process sample at a concentration from greater than 0 ppm to less than about 1 ppm.

In one aspect, the sample can be a liquid sample or a solid sample, or a combination thereof. In a further aspect, the sample comprises urea. In a still further aspect, the urea-comprising sample can comprise any liquid comprising urea in a dissolved, dispersed or liquid form. In a yet further aspect, the liquid can be a urea-comprising solution, a urea-comprising slurry or a urea-comprising melt. In an even further aspect, the urea-comprising sample can comprise urea-comprising particles or urea-comprising granules.

In one aspect, the sample comprises at least one impurity. In a further aspect, the at least one impurity can comprise ammonia, $CO_2$, or dust, or a combination thereof. In a still further aspect, the at least one impurity is ammonia, or $CO_2$, or a combination thereof In a further aspect, the sample can comprise other substances or be a mixture of urea with one or more other substances. In a still further aspect, the amount of urea in the sample can comprise from greater than 0 wt % to about 100 wt %, including exemplary wt % values of 1, 5, 10, 15, 20, 25, 30, 35, 40, 45, 50, 55, 60, 65, 70, 75, 80, 85, 90, and 95 wt %. In further aspects, the weight percentage can be in a range derived from any two of the above listed exemplary values. For example, the urea content can range from 1.5 wt % to 99.5 wt %.

In a further aspect, the sample comprises greater than about 30 wt % ammonia ($NH_3$). In a still further aspect, the sample of comprises from greater than 0 wt % to about 35 wt % ammonia, including exemplary values of 1.5 wt %, 2 wt %, 4 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 19.5 wt %, 20 wt %, 21 wt %, 22 wt %, 23 wt %, 24 wt %, 25 wt %, 26 wt %, 27 wt %, 28 wt %, and 29 wt %. In further aspects, the weight percentage can be in a range derived from any two of the above listed exemplary values. For example, the ammonia content can range from 1.5 wt % to 29.5 wt %.

In a further aspect, the sample comprises greater than 0 wt % to about 40 wt % carbon dioxide ($CO_2$), including exemplary values of 1.5 wt %, 2 wt %, 4 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 19.5 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, and 39 wt %. In further aspects, the weight percentage can be in a range derived from any two of the above listed exemplary values. For example, the ammonia content can range from 0.5 wt % to 39.5 wt %.

In a further aspect, the sample comprises sulfur. In a still further aspect, the sulfur content of the sample can be expressed as the wt % sulfate or ppm sulfate. In a yet further aspect, the sulfate can comprise calcium sulfate or ammonium sulfate, or a combination thereof. In an even further aspect, the sulfur content can overlap with the other disclosed contents.

In a further aspect, the sulfur is present as a sulfate. In a still further aspect, the sample comprises greater than about 0.02 ppm sulfate. In a still further aspect, the sample comprises greater than about 0.1 ppm sulfate. In an even further aspect, the sample comprises greater than about 1 ppm sulfate. In a yet further aspect, the sample can comprise sulfate in the range of from greater than about 0.02 ppm to about 1 ppm sulfate, including exemplary values of 0.01, 0.05, 0.1, 0.2, 0.3, 0.4, 0.5, 0.6, 0.7, 0.8, and 0.9 ppm. In further aspects, the content can be in a range derived from any two of the above listed exemplary values. For example, the sulfate can be present in the range of from 0.02 ppm to 0.9 ppm.

In one aspect, the sample can be obtained from a waste stream or a product stream, or a combination thereof. In a further aspect, the sample is obtained from a waste stream. In a still further aspect, the sample is obtained from a product stream.

In one aspect, the sample is obtained from a urea manufacturing process. In a further aspect, the sample is obtained from a urea manufacturing process. In a yet further aspect, the sample is obtained from a urea synthesis plant. In a still further aspect, the sample is obtained from a urea synthesis section.

In a further aspect, the sample is obtained from a urea granulation device. In a still further aspect, the sample is obtained from a urea granulation section. In a yet further aspect, the sample is a urea synthesis sample. In an even further aspect, the sample is a urea granule.

In a further aspect, the sulfate concentration is determined using mathematical analysis. In a still further aspect, the sulfate concentration is determined using a dilution factor calculation. In a yet further aspect, the dilution factor is represented by the equation, $$\text{Sulfate (ppm)}: \frac{SO_4 \text{ in ppm from } IC \times \text{Volume make up}}{\text{Weight/volume of sample}}.$$

In a further aspect, the sulfate concentration is determined using ion chromatography. In a still further aspect, the ion chromatography comprises ion chromatography with conductivity detector after chemical suppression. In a yet further aspect, the ion chromatography is performed using a Metrohm 819 IC or Metrohm 850 professional IC. In an even further aspect, the ion chromatography is performed using a 6.1006.100 Metrosep Anion Dual 2 column. In a still further aspect, the ion chromatography is performed using an eluent system comprising a mixture of NaHCO3, Na2CO3, and acetone.

In one aspect, the present methods are capable of determining the presence of a sulfate concentration present in an amount less than about 1 ppm. In a further aspect, the present methods are capable of determining the presence of a sulfate concentration present in an amount less than about 0.1 ppm. In a still further aspect, the present methods are capable of determining the presence of a sulfate concentration present in an amount less than about 0.02 ppm. In a yet further aspect, the present methods are capable of determining the presence of a sulfate concentration present in an amount greater than 0 ppm to about 1 ppm.

In a further aspect, the analyzing step is capable of determining the presence of a sulfate concentration present in an amount less than about 0.1 ppm. In a still further aspect, the analyzing step is capable of determining the presence of a sulfate concentration present in an amount less than about 0.02 ppm. In a yet further aspect, the analyzing step is capable of determining the presence of a sulfate concentration present in an amount greater than 0 ppm to about 1 ppm.

In a further aspect, the sample is filtered prior to concentrating to remove one or more impurities. In a still further aspect, the sample is filtered prior to concentrating to remove suspended particles. In a yet further aspect, the liquid sample of step a) is filtered prior to concentrating to remove one or more impurities. In an even further aspect, the liquid sample of step a) is filtered prior to concentrating to remove suspended particles. In a still further aspect, the sample is filtered using 0.45 micron filter paper. In a yet further aspect, the method does not comprise neutralizing a sample with an acid.

In a further aspect, at least a portion of the sample is evaporated under conditions effective to reduce the sample volume. In a still further aspect, at least a portion of the liquid sample is evaporated under conditions effective to reduce one or more impurities.

In a further aspect, the sample is subjected to conditions effective to reduce the liquid volume. In a still further aspect, conditions effective to reduce the liquid volume comprise substantially removing all moisture from the liquid sample. In a yet further aspect, conditions effective to reduce the liquid volume comprise reducing the liquid volume by at least about 1%, 5%, 10%, 20%, 30%, 40%, or 50%. In an even further aspect, conditions effective to reduce the liquid volume comprises reducing the weight of the liquid sample by at least about 1%, 5%, 10%, 20%, 30%, 40%, or 50%.

In a further aspect, conditions effective to reduce the liquid volume comprise heating the liquid sample in an air oven. In a still further aspect, conditions effective to reduce the liquid volume comprise subjecting the liquid sample to a temperature of at least about 50° C. In a yet further aspect, the oven temperature can be in the range of from about 50° C. to about 150° C., including exemplary values 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., and 145° C. In further aspects, the oven temperature can be in a range derived from any two of the above listed exemplary temperatures. For example, the granulation operating temperature can be in the range of from 90° C. to 110° C.

In further aspect, the sample can have any desired residence time in the oven effective to reduce the liquid volume. In a still further aspect, the residence time can range from 1 second to about 1 day. In a yet further aspect, the residence time is about 1 minute to about 100 minutes, including exemplary values of 10, 20, 30, 40, 50, 60, 70, 80, and 90 minutes. In an even further aspect, the residence time is about 1 hour to about 10 hours, including exemplary values of 2, 3, 4, 5, 6, 7, 8, and 9 hours.

In a further aspect, conditions effective to reduce the liquid volume comprise substantially removing one or more impurities. In a still further aspect, the conditions effective to reduce the liquid volume comprises substantially removing all impurities. In a yet further aspect, conditions effective to reduce the liquid volume comprise substantially removing all ammonia and $CO_2$ present in the liquid sample.

In a further aspect, the concentrated liquid sample has a weight of less than about 10 grams. In a still further aspect, the concentrated liquid sample has a weight of less than about 5 grams. In a yet further aspect, the concentrated liquid sample has a weight of greater than 1 gram to about 10 grams, including exemplary weights of 2, 3, 4, 5, 6, 7, 8, and 9 grams. In further aspects, the weight percentage can be in a range derived from any two of the above listed exemplary values. For example, the weight can be in the range of from 2 grams to 9 grams.

In a further aspect, the concentrated liquid sample comprises less than about 1 wt % ammonia. In a still further aspect, the concentrated liquid sample comprises less than about 0.1 wt % ammonia. In a yet further aspect, the concentrated liquid sample comprises from greater than 0 wt % to less than about 1 wt % ammonia, including exemplary wt % values of 0.01, 0.05, 0.1, 0.2, 0.3, 0.4, 0.5, 0.6, 0.7, 0.8, and 0.9 wt %. In further aspects, the weight percentage can be in a range derived from any two of the above listed exemplary values. For example, the ammonia can be present in the range of from 0.02 wt % to 0.9 wt %.

In a further aspect, the concentrated liquid sample comprises less than about 1 wt % $CO_2$. In a still further aspect, the concentrated liquid sample comprises less than about 0.1 wt % $CO_2$. In a yet further aspect, the concentrated liquid sample comprises from greater than 0 wt % to less than about 1 wt % $CO_2$, including exemplary wt % values of 0.01, 0.05, 0.1, 0.2, 0.3, 0.4, 0.5, 0.6, 0.7, 0.8, and 0.9 wt %. In further aspects, the weight percentage can be in a range derived from any two of the above listed exemplary values. For example, the $CO_2$ can be present in the range of from 0.02 wt % to 0.9 wt %.

In a further aspect, the dilute sample solution comprises greater than about 1 wt % urea. In a still further aspect, the dilute solution comprises greater than about 5 wt % urea. In a yet further aspect, the dilute sample solution comprises greater than about 1 wt % to about 10 wt % urea, including exemplary wt % values of 2, 3, 4, 5, 6, 7, 8, and 9 wt %. In further aspects, the weight percentage can be in a range derived from any two of the above listed exemplary values. For example, the urea can be present in the range of from 2 wt % to 9 wt %.

In a further aspect, the dilute sample solution comprises less than about 1 wt % ammonia. In a still further aspect, the dilute sample solution comprises less than about 0.1 wt % ammonia. In a yet further aspect, the dilute sample solution comprises from greater than 0 wt % to less than about 1 wt % ammonia, including exemplary wt % values of 0.01, 0.05, 0.1, 0.2, 0.3, 0.4, 0.5, 0.6, 0.7, 0.8, and 0.9 wt %. In further aspects, the weight percentage can be in a range derived from any two of the above listed exemplary values. For example, the ammonia can be present in the range of from 0.02 wt % to 0.9 wt %.

In a further aspect, the dilute sample solution comprises less than about 1 wt % $CO_2$. In a still further aspect, the dilute sample solution comprises less than about 0.1 wt % $CO_2$. In a yet further aspect, the dilute sample solution comprises from greater than 0 wt % to less than about 1 wt % $CO_2$, including exemplary wt % values of 0.01, 0.05, 0.1, 0.2, 0.3, 0.4, 0.5, 0.6, 0.7, 0.8, and 0.9 wt %. In further aspects, the weight percentage can be in a range derived from any two of the above listed exemplary values. For example, the $CO_2$ can be present in the range of from 0.02 wt % to 0.9 wt %.

C. Aspects

The disclosed inventions include at least the following aspects.

Aspect 1: A method, comprising:
a. providing a liquid sample comprising urea and at least one impurity;
b. concentrating the liquid sample under conditions effective to reduce the liquid volume;
c. forming a dilute sample solution by diluting the concentrated liquid sample of step b) in water; and
d. analyzing the dilute sample solution of step c) with ion chromatography to determine if a concentration of sulfate is present in the provided liquid sample of step a);
wherein the analyzing of step d) is capable of determining the presence of a sulfate concentration present in an amount less than about 1 ppm.

Aspect 2: A method, comprising:
a. providing a solid sample comprising urea and at least one impurity;
b. forming a dilute sample solution by dissolving the solid sample of step a) in water; and
c. analyzing the dilute sample solution of step b) with ion chromatography to determine if a concentration of sulfate is present in the provided solid sample of step a);
wherein the analyzing of step c) is capable of determining the presence of a sulfate concentration present in an amount less than about 1 ppm.

Aspect 3: The method of aspect 1 or 2, wherein the at least one impurity comprises ammonia, $CO_2$, or dust, or a combination thereof.

Aspect 4: The method of aspect 3, wherein the at least one impurity is ammonia, or $CO_2$, or a combination thereof.

Aspect 5: The method of aspect 1, wherein the sample of step a) is obtained from a waste stream.

Aspect 6: The method of aspect 2, wherein the sample of step a) is obtained from a product stream.

Aspect 7: The method of aspect 1 or 2, wherein the sample of step a) is obtained from a urea manufacturing process.

Aspect 8: The method of aspect 1 or 2, wherein the sample of step a) is obtained from a urea synthesis plant.

Aspect 9: The method of aspect 1, wherein the sample of step a) is obtained from a urea synthesis section.

Aspect 10: The method of aspect 1, wherein the sample of step a) is a urea synthesis sample.

Aspect 11: The method of aspect 2, wherein the sample of step a) is obtained from a urea granulation device.

Aspect 12: The method of aspect 2, wherein the sample of step a) is obtained from a urea granulation section.

Aspect 13: The method of aspect 2, wherein the sample of step a) is a urea granule.

Aspect 14: The method of aspect 1 or 2, wherein the sulfate concentration is determined using a dilution factor calculation.

Aspect 15: The method of aspect 14, wherein the dilution factor is represented by the equation $$\text{Sulfate (ppm)}: \frac{\text{SO4 in ppm from } IC \times \text{Volume make up}}{\text{Weight/volume of sample}}.$$

Aspect 16: The method of aspect 1 or 2, wherein ion chromatography comprises ion chromatography with conductivity detector after chemical suppression.

Aspect 17: The method of aspect 1 or 2, wherein ion chromatography is performed using a Metrohm 819 IC or Metrohm 850 professional IC.

Aspect 18: The method of aspect 1 or 2, wherein ion chromatography is performed using a 6.1006.100 Metrosep Anion Dual 2 column.

Aspect 19: The method of aspect 1 or 2, wherein ion chromatography is performed using an eluent system comprising a mixture of NaHCO3, Na2CO3, and acetone.

Aspect 20: The method of aspect 1, wherein the analyzing of step d) is capable of determining the presence of a sulfate concentration present in an amount less than about 0.1 ppm.

Aspect 21: The method of aspect 1, wherein the analyzing of step d) is capable of determining the presence of a sulfate concentration present in an amount less than about 0.02 ppm.

Aspect 22: The method of aspect 2, wherein the analyzing of step c) is capable of determining the presence of a sulfate concentration present in an amount less than about 0.1 ppm.

Aspect 23: The method of aspect 2, wherein the analyzing of step c) is capable of determining the presence of a sulfate concentration present in an amount less than about 0.02 ppm.

Aspect 24: The method of aspect 1, wherein the liquid sample of step a) is filtered prior to concentrating to remove one or more impurities.

Aspect 25: The method of aspect 1, wherein the liquid sample of step a) is filtered prior to concentrating to remove suspended particles.

Aspect 26: The method of aspect 1, wherein at least a portion of the liquid sample is evaporated under conditions effective to reduce one or more impurities.

Aspect 27: The method of aspect 24, wherein the liquid sample is filtered using 0.45 micron filter paper.

Aspect 28: The method of aspect 1, wherein conditions effective to reduce the liquid volume comprises substantially removing all moisture from the liquid sample.

Aspect 29: The method of aspect 1, wherein conditions effective to reduce the liquid volume comprises reducing the liquid volume by at least about 40%.

Aspect 30: The method of aspect 1, wherein conditions effective to reduce the liquid volume comprises reducing the weight of the liquid sample by at least about 40%.

Aspect 31: The method of aspect 1, wherein conditions effective to reduce the liquid volume comprises heating the liquid sample in an air oven.

Aspect 32: The method of aspect 1, wherein conditions effective to reduce the liquid volume comprises subjecting the liquid sample to a temperature of at least about 100° C.

Aspect 33: The method of aspect 1, wherein conditions effective to reduce the liquid volume comprises substantially removing one or more impurities.

Aspect 34: The method of aspect 1, wherein conditions effective to reduce the liquid volume comprises substantially removing all impurities.

Aspect 35: The method of aspect 1, wherein conditions effective to reduce the liquid volume comprises substantially removing all ammonia and $CO_2$ present in the liquid sample.

Aspect 36: The method of aspect 1, wherein the concentrated liquid sample of step b) is less than about 10 grams.

Aspect 37: The method of aspect 1, wherein the concentrated liquid sample of step b) comprises less than about 1 wt % ammonia.

Aspect 38: The method of aspect 1, wherein the concentrated liquid sample of step b) comprises less than about 0.1 wt % ammonia.

Aspect 39: The method of aspect 1, wherein the concentrated liquid sample of step b) comprises less than about 1 wt % $CO_2$.

Aspect 40: The method of aspect 1, wherein the concentrated liquid sample of step b) comprises less than about 0.1 wt % $CO_2$.

Aspect 41: The method of aspect 1 or 2, wherein the dilute sample solution comprises greater than about 1 wt % urea.

Aspect 42: The method of aspect 1 or 2, wherein the dilute solution comprises greater than about 5 wt % urea.

Aspect 43: The method of aspect 1 or 2, wherein the dilute sample solution comprises greater than about 1 wt % to about 10 wt % urea.

Aspect 44: The method of aspect 1 or 2, wherein the dilute sample solution comprises less than about 1 wt % ammonia.

Aspect 45: The method of aspect 1 or 2, wherein the dilute sample solution comprises less than about 0.1 wt % ammonia.

Aspect 46: The method of aspect 1 or 2, wherein the dilute sample solution comprises greater than about 0.1 wt % $CO_2$.

Aspect 47: The method of aspect 1 or 2, wherein the dilute sample solution comprises greater than about 0.1 wt % $CO_2$.

Aspect 48: The method of aspect 1, wherein the sample of step a) comprises greater than about 30 wt % ammonia.

Aspect 49: The method of aspect 1, wherein the sample of step a) comprises from greater than 0 wt % to about 35 wt % ammonia.

Aspect 50: The method of aspect 1, wherein the sample of step a) comprises greater than 0 wt % to about 40 wt % $CO_2$.

Aspect 51: The method of any preceding aspect, wherein the method does not comprise neutralizing a sample with an acid.

Aspect 52: A method, comprising:
a. providing a process sample comprising urea and sulfate; and
b. analyzing the process sample with ion chromatography to determine the sulfate concentration in the process sample; wherein analyzing of step b) can determine sulfate concentration present in the process sample at a concentration from greater than 0 ppm to less than about 1 ppm.

Aspect 53: The method of aspect of 52, wherein the process sample comprises at least one impurity.

Aspect 54: The method of aspect of 53, wherein the at least one impurity comprises ammonia, or $CO_2$, or dust, or a combination thereof.

Aspect 55: The method of aspect of 53, wherein the at least one impurity comprises ammonia, or $CO_2$, or a combination thereof Aspect 56: The method of aspect of 52, wherein the process sample is obtained from a waste stream or a product stream, or a combination thereof Aspect 57: The method of aspect of 52, wherein the process sample is obtained from a urea manufacturing process.

Aspect 58: The method of aspect of 52, wherein the process sample is obtained from a urea granulation device.

Aspect 59: The method of aspect of 52, wherein the process sample is obtained from an acid or ammonia scrubber.

Aspect 60: The method of aspect of 52, wherein the process sample is obtained from a urea synthesis plant.

Aspect 61: The method of aspect of 52, wherein the sulfate concentration is determined using a dilution factor.

Aspect 62: The method of aspect of 61, wherein the dilution factor is represented by the equation $$\text{Sulfate (ppm)}: \frac{\text{SO4 in ppm from } IC \times \text{Volume make up}}{\text{Weight/volume of sample}}.$$

Aspect 63: The method of aspect of 52, wherein ion chromatography comprises ion chromatography with conductivity detector after chemical suppression.

Aspect 64: The method of aspect 52, wherein the analyzing of step c) is capable of determining the presence of a sulfate concentration present in an amount less than about 0.1 ppm.

Aspect 65: The method of aspect 52, wherein the analyzing of step c) is capable of determining the presence of a sulfate concentration present in an amount less than about 0.02 ppm.

D. Experimental

The following examples are put forth so as to provide those of ordinary skill in the art with a complete disclosure and description of how the compositions and/or methods claimed herein are made and evaluated, and are intended to be purely exemplary of the invention and are not intended to limit the scope of what the inventors regard as their invention. Efforts have been made to ensure accuracy with respect to numbers (for example, amounts and temperatures), but some errors and deviations should be accounted for. Unless indicated otherwise, parts are parts by weight, temperature is in ° C. or is at ambient temperature, and pressure is at or near atmospheric.

Several methods for preparing the compositions of the present invention are illustrated in the following examples. Starting materials and the requisite intermediates are in some cases commercially available, or can be prepared according to literature procedures or as illustrated herein.

The following exemplary compositions of the invention were prepared. The examples are provided herein to illustrate the invention, and should not be construed as limiting the invention in any way.

1. General Methods

All materials and reagents were used as is unless otherwise indicated.

Ion chromatography analysis was performed using the following instrument, column, and eluents:

Instrument: Metrohm 819 IC

Column: 6.1006.100 Metrosep Anion Dual 2

Eluent: 2.0 mmol/L (0.3360 g/2 L) Sodium Hydrogen Carbonate (NaHCO3)+1.3 mmol/L (0.2756 g/2 L) Sodium Carbonate (Na2CO3)+5% (100 ml/2 L) Acetone.

Suppressor: Metrohm suppressor Module (MSM, 50 mmol/L, H2SO4)

Instrument, eluent & suppressor were prepared per manufacturer recommendations. Column and guard column were installed as per manufacturer recommendation. IC instrument settings were:

Column Flow: 0.8 ml/min

Injection Volume: 100

For preparation of calibration curve as shown in FIG. 1, sulfate standards of 0.005, 0.01, 0.050, 0.10, 0.20, 0.35 and 0.50 ppm were prepared from stock solution (1000 ppm SO4 prepared from ammonium sulfate AR grade). The instrument was then run for stable base line. Next, the instrument was calibrated using ultrapure water and prepared calibration standards.

The method was then prepared for quantification using the above standards. Following calibration, verify calibration curve is within acceptable range for RSD and correlation co-efficient. If the calibration curve is in range, the unknown sample can then be run. If the sulfate concentration is found to be more than the calibration range, the sample can be diluted and run again.

After the sample is analyzed, the final results are calculated using the dilution factor calculation:

$$\text{Sulfate (ppm)}: \frac{SO_4 \text{ in ppm from } IC \times \text{Volume make up}}{\text{Weight/volume of sample}}.$$

The factor for conversion $SO_4$ to ammonium sulfate is 1.375.

In various aspects, samples that can be tested using the methods of the present invention can have exemplary sample descriptions and compositions as shown in Table 1.

TABLE 1

| Sample Description | Urea % | Ammonia % | CO$_2$ % |
|---|---|---|---|
| Urea Reactor | 33.5-35.0 | 28.5-30.5 | 17.0-18.5 |
| Stripper Output | 53.3-55.3 | 6.42-8.5 | 6.3-9.98 |
| Rectifying Column | 67.0-69.0 | 2.0-2.8 | 0.9-1.3 |
| Low Pressure Carbamate Condensate (LPCC) | 0.1 | 29.5-31.5 | 37-39 |
| Urea Solution Tank | 0.08 | 78-79.5 | 0.08 |
| Urea Granulation Scrubber | 43-46 | 1000 ppm | 800 range |
| Urea Recycle Tank | 43-46 | 1000 ppm | 800 range |
| Urea Granule Product | 100 ppm | Max 100 ppm | — |

2. Example 1

In Example 1, a sample having a high urea content, low NH3 content, and low CO2 content is prepared for testing to determine sulfate concentration according to the present methods.

First, the raw sample to tested is filtered through 0.45 micron Millipore filter paper. Next, 10-15 grams of the filtered sample is weighed in a beaker. Next, the weighed sample in placed in a 110° C. air oven until the sample has evaporated to dryness. The dried sample is allowed to cool, and then dissolved in sufficient ultrapure water to bring the total volume to 100 ml. The prepared, dilute sample solution is then analyzed using the analytical methods described herein to determine the sulfate content.

3. Example 2

In Example 2, a sample having a high NH3 content and high $CO_2$ content is prepared for testing to determine sulfate concentration according to the present methods.

First, the raw sample is filtered through 0.45 micron Millipore filter paper. Next, 8-12 grams of the filtered sample is weighed in a beaker. Next, the weighed sample in placed in a 110° C. air oven until the sample has evaporated to dryness. The dried sample is allowed to cool, and then dissolved in sufficient ultrapure water to bring to the total volume to 100 ml. The prepared, dilute sample solution is then analyzed using the analytical methods described herein to determine the sulfate content.

4. Example 3

In Example 3, a sample of urea granule product is prepared for testing to determine sulfate concentration according to the present methods.

8-9 grams of raw sample is weighed, and dissolved in sufficient ultrapure water to bring the total volume to 100 ml (maximum concentration of the diluted sample solution should not exceed 10% urea by weight). The diluted sample solution is then allowed to normalize to room temperature. The prepared, dilute sample solution is then analyzed using the analytical methods described herein to determine the sulfate content.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method, comprising:
a. obtaining a liquid sample comprising at least one impurity and comprising urea at 5 wt. % or greater based on total weight of the liquid sample;

b. concentrating the liquid sample under conditions effective to reduce the liquid volume and increase the concentration of the urea in the liquid sample;

c. forming a dilute sample solution by diluting the concentrated liquid sample of step b) in water; and d. analyzing the dilute sample solution of step c) with ion chromatography to determine if a concentration of sulfate is present in the obtained liquid sample of step a);

wherein the analyzing of step d) is capable of determining the presence of a sulfate concentration present in an amount less than 1 ppm.

2. The method of claim 1, wherein the analyzing of step d) comprises performing the ion chromatography using an eluent comprising a mixture of $NaHCO_3$, $Na_2CO_3$, and acetone.

3. The method of claim 1, wherein the analyzing of step d) comprises determining the presence of a sulfate concentration present in an amount less than 0.1 ppm.

4. The method of claim 1, wherein the analyzing of step d) comprises determining the presence of a sulfate concentration present in an amount less than 0.02 ppm.

5. The method of claim 1, wherein the liquid sample of step a) is filtered prior to concentrating the liquid sample in step b), wherein the filtering removes at least one of the at least one impurity.

6. The method of claim 1, wherein the liquid sample of step a) further includes suspended particles, and the method further comprises filtering the liquid sample of step a) prior to concentrating the liquid sample in step b), wherein the filtering removes the suspended particles.

7. The method of claim 1, wherein conditions effective to reduce the liquid volume comprises subjecting the liquid sample to a temperature of at least 100° C.

8. The method of claim 1, wherein conditions effective to reduce the liquid volume comprises substantially removing one or more impurities.

9. The method of claim 1, wherein conditions effective to reduce the liquid volume comprises substantially removing all impurities.

10. The method of claim 1, wherein conditions effective to reduce the liquid volume comprises substantially removing all ammonia and $CO_2$ present in the liquid sample.

11. The method of claim 1, wherein the method does not comprise neutralizing the liquid sample with an acid.

12. The method of claim 1, wherein obtaining the liquid sample in step a) obtains a liquid sample comprising the urea and the at least one impurity, wherein the at least one impurity comprises ammonia, $CO_2$, or dust, or a combination thereof.

13. The method of claim 12, wherein obtaining the liquid sample in step a) obtains a liquid sample comprising the urea and the at least one impurity, wherein the at least one impurity is ammonia, or $CO_2$, or a combination thereof.

14. The method of claim 1, wherein the analyzing in step d) of the sulfate concentration comprises using a dilution factor calculation.

15. The method of claim 14, wherein the dilution factor calculation used in step d) is:

Weight or volume of the dilute sample solution ÷ Weight or volume of liquid sample.

16. A method, comprising:

a. obtaining a solid sample comprising at least one impurity and comprising urea at 5 wt. % or greater based on total weight of the solid sample;

b. forming a dilute sample solution by dissolving the solid sample of step a) in water; and c. analyzing the dilute sample solution of step b) with ion chromatography to determine if a concentration of sulfate is present in the obtained solid sample of step a);

wherein the analyzing of step c) is capable of determining the presence of a sulfate concentration present in an amount less than 1 ppm.

17. The method of claim 16, wherein obtaining the solid sample of step a) comprises obtaining a urea granule.

18. A method, comprising:

a. obtaining a process sample comprising sulfate and comprising urea at 5 wt. % or greater based on total weight of the process sample; and b. analyzing the process sample with ion chromatography to determine the sulfate concentration in the process sample;

wherein the analyzing of step b) is capable of determining a sulfate concentration present in the process sample at a concentration from greater than 0 ppm to less than 1 ppm.

19. The method of claim of 18, wherein obtaining the process sample in step a) comprises obtaining a process sample further comprising at least one impurity.

20. The method of claim of 19, wherein obtaining the process sample in step a) comprises obtaining the process sample comprising the at least one impurity, the at least one impurity comprising ammonia, or $CO_2$, or dust, or a combination thereof.

* * * * *